United States Patent [19]

Carey et al.

[11] 3,960,153
[45] June 1, 1976

[54] APPARATUS FOR THE PALLIATIVE TREATMENT OF PLEURAL EFFUSIONS

[76] Inventors: Jane Towne Carey, 1161 York Ave., New York; Alfred Andrew Fracchia, 440 E. 63 St., Plandome, both of N.Y. 10021

[22] Filed: Feb. 22, 1972

[21] Appl. No.: 227,713

Related U.S. Application Data

[63] Continuation-in-part of Ser. No. 862,434, Sept. 30, 1969, abandoned.

[52] U.S. Cl. ............................ 128/347; 128/350 R
[51] Int. Cl.² .................. A61B 17/34; A61M 27/00
[58] Field of Search ............ 128/214.4, 8, 347, 348, 128/349 R, 350 R

[56] References Cited
UNITED STATES PATENTS

| | | | |
|---|---|---|---|
| 1,736,182 | 11/1929 | Wilkins | 128/350 R |
| 2,930,378 | 3/1960 | Buyers | 128/350 R |
| 3,058,472 | 10/1962 | Thornton, Jr. | 128/348 |
| 3,189,031 | 6/1965 | Andersen | 128/350 R |
| 3,370,587 | 2/1968 | Vizcarra | 128/348 X |
| 3,395,710 | 8/1968 | Stratton et al. | 128/350 R |
| 3,653,388 | 4/1972 | Tenckhoff | 128/347 |

FOREIGN PATENTS OR APPLICATIONS

| | | | |
|---|---|---|---|
| 1,482,481 | 4/1967 | France | 128/8 |

*Primary Examiner*—Channing L. Pace

[57] ABSTRACT

To withdraw pleural effusions from between the visceral and parietal pleurae, which accumulate due to metastatic carcinoma of the breast, a catheter is inserted into the fluid accumulation which is withdrawn through the catheter by a suction device. The catheter has a weighted end which can be magnetically manipulated. The catheter is provided with specially shaped and located openings to take into account the fluid's high content of insoluble, coagulable strands of fibrin.

12 Claims, 6 Drawing Figures

APPARATUS FOR THE PALLIATIVE TREATMENT OF PLEURAL EFFUSIONS

OTHER APPLICATIONS

This is a continuation-in-part of our copending application, Ser. No. 862,434, filed Sept. 30, 1969 now abandoned.

BACKGROUND

As a basis for understanding the problems with which the present invention is involved, reference is made to the following definition by Robert P. Morehead in Human Pathology, the Blakiston Division, McGraw-Hill Book Co., New York, 1965, Page 1507.

Serofibrinous Pleuritis (Pleurisy with effusion); a detectable exudate within the pleural cavity indicates rather extensive pleural involvement by infection, tumor or pulmonary infarction. Of the etiologic factors, infection in contiguous structures particularly pulmonary tuberculosis is by far the most important in persons under forty; in later years, cancer is the most important. Dyspnea and pain on inspiration are the principal symptoms. Since the visceral pleura is insensitive, pain is due to involvement of the parietal pleura and adjacent tissues. Dyspnea results when a large volume of fluid encroaches on the lung or when motion of the chest is restricted because of severe pain. X-ray examination will confirm the physical findings indicating fluid in the chest. Examination of pleural fluid obtained by thoracentesis gives the most accurate information as to the true nature of the effusion. Exudates may be differentiated from transudates by determining the specific gravity and total protein content of the fluid. Exfoliative cytology may be helpful in establishing the cause of those cases in which the effusion is secondary to a malignant tumor.

Stanley L. Robbins in Textbook of Pathology, W. B. Saunders Co., Philadelphia, 1964, Page 595 further adds: "It is frequently quite important to be able to differentiate a serous or serofibrinous exudate of inflammatory origin from a simple transudate of circulatory origin. In general, the serofibrinous exudates consist of relatively clear, limpid, straw-colored fluid in which, occasionally, small strands of opaque, yellow-white fibrin may be found floating. The specific gravity of these fluids tends, on the whole, to be greater than 1.016 to 1,020 and frequently, by centrifugation, scattered lymphocytes, macrophages, and a few polymorphonuclear neutrophiles, as well as the ever-present mesothelial cells, can be found within the sediment."

The total protein content of such exudates is greater than 0.6 mg. protein /100 ml. and is usually greater than 3.0 gm. protein /100 ml.

In the cases with which the present invention is concerned, large volumes of serofibrinous or bloody fluid are present. The volume obtained may range from 600 ml. to more than two liters. These effusions tend to recur in corresponding volumes at an early date when treated only by standard thoracentesis, necessitating repeated hospitalizations and additional tappings.

SUMMARY OF INVENTION

We have come to believe that perhaps one reason for early reaccumulations of fluid was the fact that it was not possible to remove all pleural fluid with the materials and methods available. Accordingly, we have developed a weighted catheter to insure the removal of all metastatic fluid so that the compressed lung can expand downwardly and so that the pleural surfaces can coapt and adhere.

Because of the high content of insoluble, coagulable strands of fibrin and, in some instances, blood, exact specifications, particularly for the holes in the tubing, are critical. From earlier cases which were treated, difficulties were encountered due to the fact that the size and shape of the holes in the catheters employed had not been properly calculated, resulting in plugging of the holes. Since these errors have been corrected the results have been excellent with no blockage whatsoever, even though the effusions were some times hemorrhagic and thrombotic.

The technique for our procedure is simple. A small skin incision is made under local anesthesia (1% procaine or the equivalent) in the intercostal space indicated by the fluid level. The trocar is then introduced into the intercostal space. In order to avoid damage to the intercostal vessels and nerves, the trocar is kept as close as possible to the upper edge of the lower rib. The obturator of the trocar is then removed, and the weighted catheter is introduced through a Teflon sleeve. When the desired depth is reached, the Teflon sleeve is removed, the catheter is affixed to the skin by sutures and the proximal end of the catheter is attached either to underwater seal drainage or to suction.

Pre- and post-treatment X-rays are taken. The catheter must remain in place for a minimum of two days or until no further fluid is obtained. Frequent chest X-rays are taken while the catheter is in place. After the weighted tube is removed, chest X-rays are taken at intervals chosen by the physician.

From the above, it will be seen that an object of the invention is to provide an improved technique for the removal of pleural accumulations.

Yet another object of the invention is to provide improved apparatus enabling the method of the invention to be practiced effectively.

Said apparatus, according to a preferred embodiment of the invention, includes, in addition to a trocar permitting insertion of the device, a catheter having a magnetically manipulatable weighted end and provided with a special arrangement of specially designed elliptical openings which prevent clogging by fibrin and the like. The details of these openings will be disclosed hereinafter.

A further advantage is that it is possible to instill chemotherapeutic agents such as $HN_2$ or thio-TEPA or radioactive isotopes such as $P^{32}$ through the tube, clamp the tube for 4–6 hours and then reinstitute suction. Such a method will aid in the creation of adhesions between the visceral and parietal pleurae.

PRIOR ART

Catheters or tubes having non-circular openings are known. Some of these are disclosed, for example, in U.S. Pat. Nos. 3,314,430; 3,189,031; 3,384,089. These known devices, however, are not suitable for the removal of pleural fluids since they do not take into account the location and design of the special openings essential to prevent blockage by fibrin and the like.

Weighted catheters or tubes are also known such as, for example, the device disclosed in U.S. Pat. No. 2,853,075. Such known devices also fail to take into account the particular environmental problems dealt with by the present invention.

It is also known to employ magnets within bodies such as the use of a magnet disclosed by R. D. Hoffman in U.S. Pat. No. 2,853,075. Insofar as we known, however, the use of magnetic attraction in the removal of pleural fluids and in the manner which we set forth below is both new and useful and unanticipated by prior patents or publications.

DRAWING

DETAILED DESCRIPTION

As has been noted hereinabove the method of the invention is comparatively simple. It initially involves a small skin incision made while the patient is under the effect of a local anesthetic such as, for example, 1% procaine or the equivalent. The incision is made in the intercostal space indicated by a check of the fluid level.

When the incision has been made, a trocar is introduced into the intercostal space and in order to avoid damage to the intercostal vessels and nerves the trocar is kept as close as possible to the upper edge of the lower rib.

The obturator of the trocar is then removed and a weighted catheter is introduced through a Teflon sleeve forming part of the trocar assembly.

When the desired depth of penetration is reached the sleeve is removed and the catheter is affixed to the skin by sutures. The proximal end of the catheter is then attached either to underwater seal drainage or to a suction device.

Pre-treatment and post-treatment X-rays are taken and it is found that the best results are obtained if the catheter remains in place for a minimum of four days or until no further fluid is obtained although usually the upper limit for obtaining the desired results may be considered as being six days.

Frequent chest X-rays are taken while the catheter is in position and after the weighted tube is removed chest X-rays may be taken at intervals selected by the physician.

Figure 1:
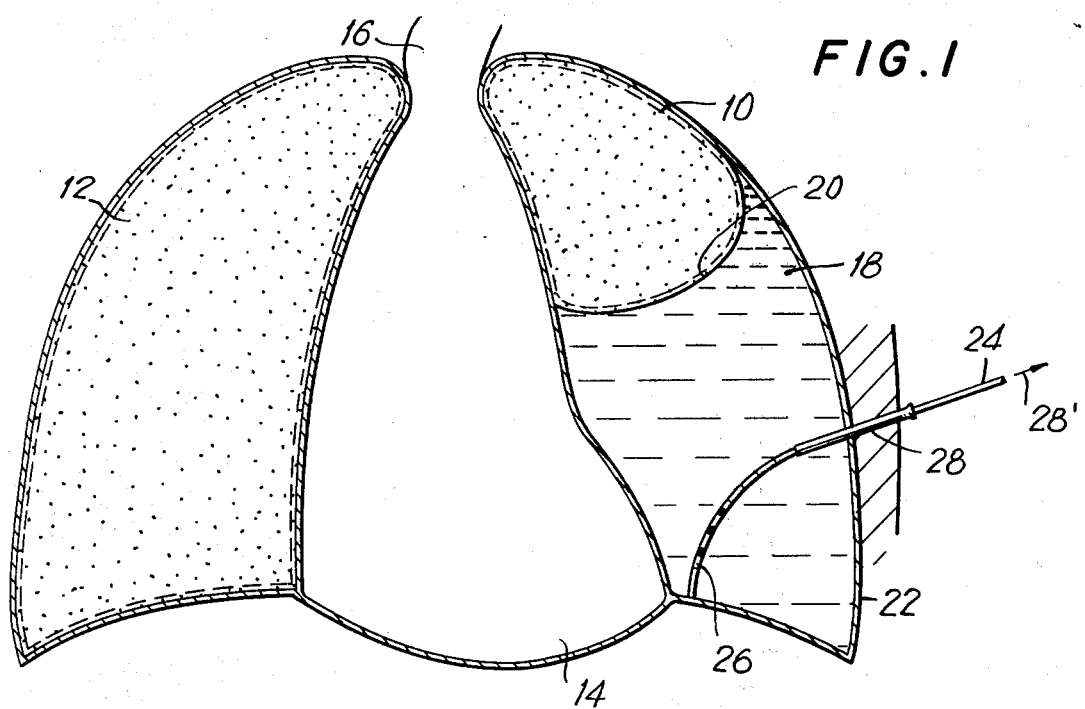
FIG. 1 is a diagrammatic illustration of the thoracic region of a human body showing an accumulation of pleural fluid and with the catheter of the invention inserted therein.

In FIG. 1 are illustrated lungs 10 and 12, the heart being diagrammatically indicated at 14 and the aorta at 16. The lung 12 is filled with normal healthy lung substance whereas the lung 10 is illustrated as being diseased. There is an accumulation of pleural fluid indicated at 18 which accumulates between the visceral pleura 20 and the parietal pleura 22.

The purpose of the invention is to provide for the removal of the fluid 18 so that the collapsed lung substance can expand whereupon the visceral pleura will reoccupy a position juxtaposed to the parietal pleura so that these two pleurae can coapt and adhere to one another. This it has been found prevents a recurrence of the accumulation of pleural fluid, particularly when used in conjunction with the injection through the tube of chemotherapeutic agents or radioisotopes.

To enable the removal of this accumulation of fluid a catheter 24 is inserted into the thoracic cavity to a position between the visceral and parietal pleurae. The catheter 24 has a weight end 26 and is inserted through a sleeve 28 forming part of a trocar assembly as will be explained in further detail hereinafter. The removal of the fluid is indicated by arrow 28' which diagrammatically indicates a connection to an underwater sealed drainage or to a suction device.

Figure 2:
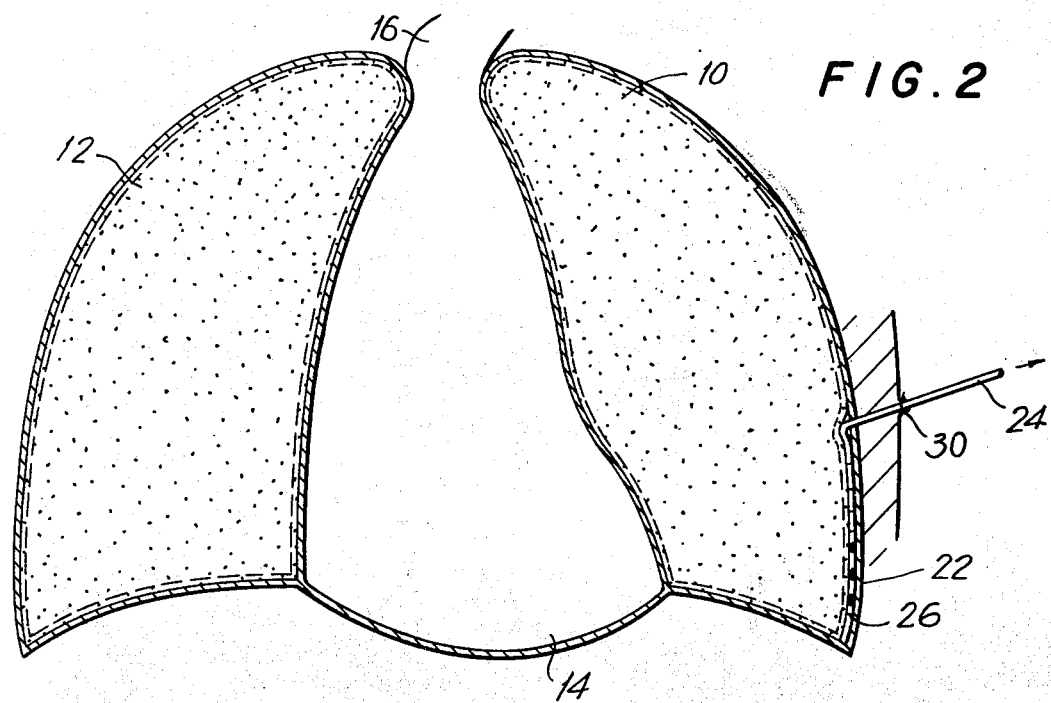
FIG. 2 is a view similar to that of FIG. 1 but with the fluid removed.

FIG. 2 illustrates the lung example of FIG. 1 with the fluid having been removed. Herein it can be seen that the lung substance of lung 10 has expanded as is permitted by the removal of the fluid 18, the catheter 24 still remaining in position with the weight 26 occupying a position at the lower righthand corner of the lung in the illustrated arrangement.

In this figure it will be noted that the catheter 24 is held in position by sutures 30 this suturing being effected after the initial insertion of the catheter.

Figure 3:
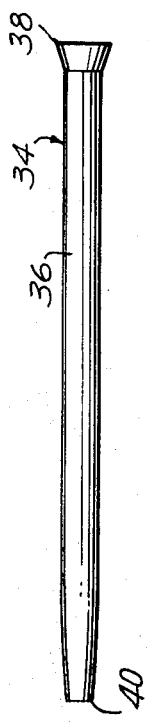
FIG. 3 is a view of a trocar sleeve employed in the insertion of the catheter into the body.

At this point in the treatment with the fluid having been removed the catheter is drawn out of the thoracic cavity and the coating and adhesion of the pleurae may then take place. Chemotherapeutic agents or radioisotopes may be instilled through the tube after the removal of all fluid.

in FIG. 3 is illustrated a Teflon trocar sleeve 34 (which is a slight variation of the sleeve 28 of FIG. 1) consisting of a tubular central portion 36 preferably tapered towards the left end and provided with a flared end 38 and a tapered end 40. The sleeve 34 has a bore extending completely therethrough for the accommodation of an obturator as will be described hereinafter.

By way of example the sleeves may have an overall length of 12.2 centimeters with a diameter of 1.25–1.35 centimeters at the flared end 38. The diameter of the tapered end 40 may be for example 0.65 centimeters – 0.75 centimeters.

Figure 4:
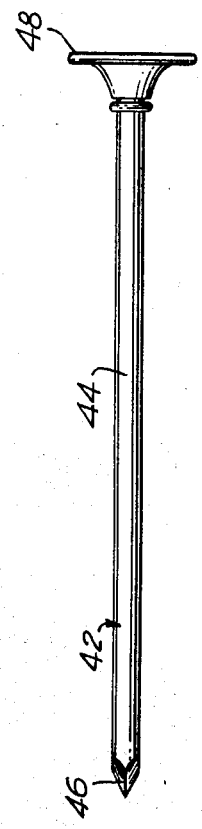
FIG. 4 is a view of a trocar obturator employed with the sleeve of FIG. 3.

As noted hereinabove the procedure of the invention is initiated by a small incision of the skin in the duly located intercostal space related to the fluid level. The sleeve is then inserted in this incision and this is accomplished by the use of the stainless steel obturator illustrated by way of example in FIG. 4. Said obturator is indicated at 42 and includes an elongated body 44 provided with a pointed tip 46 and having at the other end thereof a thumb guard 48.

This obturator is accommodated within the sleeve 34 and the assembly is forced through the incision into the cavity in which the pleural fluid has accumulated whereafter the obturator 42 is withdrawn from the sleeve 34 leaving the latter in position.

Insertion of the assembly is facilitated by the provision of the pointed tip 46 and pressure is applied to the assembly through the intermediary of the thumb guard 48.

By way of example the overall length of the obturator may, for example, be 14.0 centimeters, the diameter of the body of the obturator being for example 0.6 to 0.7 centimeters with a diameter of the thumb guard being, for example, 2.2 centimeters.

Figure 5:
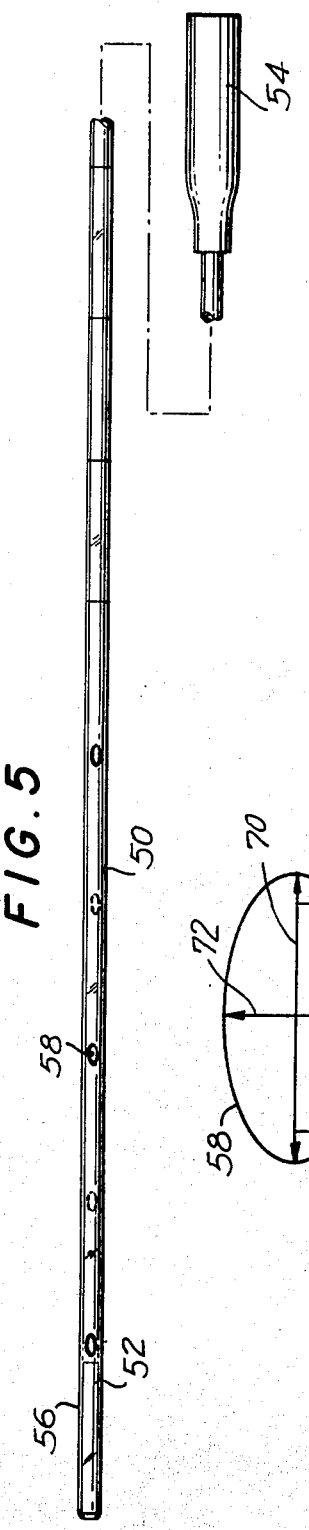
FIG. 5 illustrates a catheter of the invention with an adapter thereon.

The catheter employed in accordance with the invention is illustrated in FIG. 5 and it is inserted into the accumulated fluid through the bore of the sleeve 34 after the obturator 42 has been removed from the said sleeve.

The catheter illustrated in FIG. 5 is a weighted catheter made up of three components which quite generally are constituted by a polyvinyl tubing 50, a weight 52 and a removable plastic adapted 54.

With respect to the tubing polyvinyl is preferred because it provides the flexibility necessary for the functions to be performed. Moreover, it has been determined experimentally that this polymer expands three to sixteen thousandths of an inch at the time of initial autoclaving and the dimensions can be so adjusted that the tubing can be readily introduced through the aforenoted trocar sleeve despite repeated autoclavings.

It has been experimentally determined that all overall length of tubing of about 94 centimeters is preferred although this length can be varied in accordance with the location of the associated suction apparatus or whatever apparatus may be employed to aspirate the fluid. The outside diameter of the tubing preferably lies within the range of 6.0 to 8.0 millimeter whereas the inside diameter of the tubing preferably lies within the range of 5.0 to 7.0 millimeters. The wall thickness is generally in the order of 1.0 millimeters.

The weight 52 is preferably made of nickel-platinum alloy. This weight is encased in a chamber 56 located at the distal 3 centimeters, preferably 2.5 centimeters of the polyvinyl tubing and separated from the bore of the latter.

The material from which the weight is made is chosen based on the fact that they are unmagnetized but are attracted by and hence can be directed by a magnet applied to the external chest wall. The weight is an elongated cylinder which may be readily seen and recognized by means of X-ray techniques or the like.

As has been indicated above the length of the weight is preferably in the order of 3 centimeters but the weight which has been found to be most satisfactory lies within the range of 2.25 to 3.25 grams.

The removable plastic adapter 54 is attached to the proximal end of the catheter in order that this apparatus may be attached to underwater seal drainage or to a suction device. This adapter is detachable in order to provide for the removal of the trocar sleeve discussed hereinabove prior to the connection of the catheter to the underwater seal drainage or suction device.

By way of example, the length of the adapter may be in the range of about 4 to 4½ centimeters and the outside diameter at the distal end is 7.5 to 8.5 millimeters whereas the inside diameter at the distal end is 6.5 to 7.5 millimeters. The diameter of the adapter at the proximal end is about 9.5 millimeters externally and 8.5 millimeters internally. A wall thickness of about 1.0 millimeter has been found satisfactory.

The tubing 50 is provided with a distribution of elliptical openings or holes 58. These holes are distributed immediately proximal to the encased weight 52 and are five in number these being spaced apart at 2.5 centimeter intervals on opposite sides of the tubing with their major axes directed parallel to the longitudinal axis of the tubing.

These alternating holes extend for a distance of about 11 centimeters from the proximal end of the weight 52 and are generally much less than one-third of the length of the tubing 50.

The holes 58 must be elliptical rather than circular in shape to provide a greater surface area without weakening the tube. However more important is the fact that there is less tendency for elliptical holes to become plugged with fibrin and like matter in the fluid to be removed.

The dimensions and areas of these holes are critical for the best results and the following dimensions should be employed if superior results are desired although some tolerance in these dimensions is possible if some degree of the exceptional results of the invention can be sacrificed: Major axis: 8.0–10.0 millimeters; Minor axis: 4.0–5.0 millimeters; Distance between foci: 7.0–8.8 millimeters; Area 0.215–0.393 square centimeters.

Figure 6:
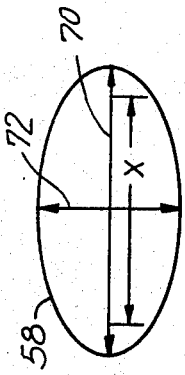
FIG. 6 illustrates the critical dimensions of the openings in said catheter.

Reference to FIG. 6 will illustrate the aforenoted dimensions so that there will be no confusion with respect thereto. Thus the hole 58 in FIG. 6 is provided with a major axis 70, a minor axis 72 and a distance X between the two foci at opposite ends of the ellipse.

In addition to the aforegoing critical arrangement of openings the tubing 50 is provided for a distance of about 12.5 centimeters proximal to the hole furthest from the weight 52 with gradations or markings at 2.5 centimeter intervals to enable the person employing the device to determine the depth to which the catheter has been inserted.

The catheter arrangement of the invention has been employed clinically and the following are notations with respect to five patients to whom the apparatus of the invention has been employed:

Patient - A - 68-26-68

3/15/69 Weighted catheter inserted with removal of 2000 ml. Partial control for three months. 6/15/69 recurrent effusion noted. Tube reinserted with removal of 1500 ml. of fluid followed by hemithorax radiation for possible lymphangitic metastases. As of 7/9/69 no recurrence of pleural fluid but increase of lymphangitic metastases.

Patient - B - 22- 55-99

Primary inoperable carcinoma of the right breast, 12/17/68 right pleural effusion. Standard thoracentesis 600 ml. removed followed by instillation of 6.5 mc P32. 5/28/69 recurrent right pleural effusion, 3400 ml. removed through weighted catheter. Patient accidentally pulled tube out 5/31/69. Reinsertion of tube on 6/1/69. 250 additional ml. removed. Catheter removed 6/10/69.

Patient - C - 60-86-42

This patient had bilateral radical mastectomies, inflammatory recurrence of the entire chest wall 11/68. 12/68 bilateral adrenalectomy —no response. 4/6/69 right pleural effusion, weighted catheter inserted with removal of 1500 ml. of metastatic fluid followed by instillation of P32. This patient was subsequently treated with Cytoxan, Clomid and 5FU, but was terminal andn died on 5/31/69. No recurrence of pleural effusion noted, Patient - D - 26-23-14

Primary inoperable carcinoma of the right breast, 6/16/69 left pleural effusion. Weighted catheter inserted and 2500 ml. of frankly hemorrhagic pleural fluid removed. Total drainage 3400 ml. When the catheter was removed there was a large thrombus in the lumen of the tube but it still continued to drain freely. The tube was removed 6/27/69. No recurrence as of 7/8/69.

Patient -E-

6/24/69 Right chest tube inserted and 1000 ml. fuild removed. However, the lung was not able to expand downward due to extensive fibrosis and scarring of the pleural. This is an excellent example of a "trapped lung" and the weighted catheter will produce no benefit in such a situation.

Catheters not provided with the critical arrangement of the invention have been previously employed in other patients as to which some notations are as follows:

Patient - F - 26-49-58

4/2/68 Weighted catheter inserted in the left pleural space with initial drainage of 1000 ml.; total drainage 1500 ml. Holes plugged with fibrin, flushed out with saline, 1600 ml. additional of metastatic fluid aspirated. 4/11/68 tube obstructed due to twisting, removed 4/13/68. This patient had no recurrence of effusion as of June, 1969.

Patient - G 27 -05-73

3/28/68 Weighted catheter inserted on right. Total drainage 2500 ml. Tube holes became plugged with fibrin. Diminution of effusion after flushing with saline and aspiration. Died of advanced disease 4/29/68.

It is apprciated that the above notations are limited in number but they are exemplary of the results which have been achieved. It should be noted that more than 100 patients have been treated in our series.

It will be noted in the apparatus disclosed above that the tubes inclusive of the chamber in which the weight is accommodated is of uniform diameter thereat.

It will also be noted that there has been disclosed an apparatus for removing fluid from a body cavity comprising an elongated flexible tube including distal and proximal ends and having at the distal end a closed chamber in which a weight is accommodated. The proximal end is adapted for being coupled to a suction source and the tube is provided with a bore extending substantially throughout the same from adjacent the aforesaid chamber to said proximal end. The wall is provided with elliptical openings distributed longitudinally along the wall of the tubes from adjacent the chamber towards the proximal ends along a length of the tube which is less than one-third the total length thereof.

As will be noted there has been disclosed above a method for the palliative treatment of pleural effusion to metastatic carcinoma of the breast resulting in the accumulation of pleural fluid between the visceral and parietal pleurae. This method comprises inserting between said pleurae the weighted end of a perforated catheter and withdrawing the fluid whereupon the pleura can coapt and adhere to another.

It has also been further disclosed the technique of inserting the catheter through the associated body wall by driving a trocar sleeve through the body wall with a pointed trocar obturator inserted in the sleeve the obturator being subsequently withdrawn leaving the sleeve in position in the body wall the catheter being introduced through the sleeve.

The catheter of the invention is manipulated internally of the body by manipulating the weighted end with the use of a magnet.

The catheter is held in position for withdrawing the fluid by suturing the catheter to the body wall and draining and whereafter the fluid is drained for a period of about two to six days and longer if required.

There will now be obvious to those skilled in the art many modifications and variations of the structures and techniques set forth hereinabove. These modifications and variations will not however depart from the scope of the invention as defined by the following claims;

What is claimed is:

1. Apparatus for removing fluid from a body cavity comprising an elongated flexible tube including distal and proximal ends and having at the distal end a closed chamber, said proximal end being adapted for being coupled to a suction source, the tube including a generally cylindrical wall provided with a bore extending substantially throughout the tube from adjacent said chamber to said proximal end, said wall being provided with elliptical openings distributed longitudinally along said wall from adjacent the chamber toward said proximal end along a length of the tube which is less than one-third the total length thereof, and a weight in said chamber, the elliptical openings being substantially the same size and having a major axis of about 8.0 to 10.0 mm., a minor axis of about 4.0 - 50 mm., a distance between foci of about 7.0 to 8.8 mm. and an area of about 0.215 to 0.393 sq. cm.

2. Apparatus as claimed in claim 1 wherein said weight is unmagnetized but is magnetically attractable for manipulation in said cavity.

3. Apparatus as claimed in claim 1 comprising means detachably coupled to the proximal end for coupling the latter to said suction source.

4. Apparatus as claimed in claim 1 comprising trocar means to insert the tube into said cavity, said trocar means including a tapered sleeve and a obturator detachably extending through and conforming to the shape of the sleeve, said obturator having a pointed end extending from the sleeve and adapted for penetrating into said cavity.

5. Apparatus as claimed in claim 1 wherein the tube inclusive of said chamber is of uniform diameter throughout.

6. Apparatus as claimed in claim 1 wherein the tube is of polyvinyl.

7. Apparatus as claimed in claim 1 wherein the weight is an elongated cylinder weighing about 1.25 to 2.25 grams.

8. Apparatus as claimed in claim 1 wherein the tube has an outside diameter of about 4.3 to 5.3 mm. and an inner diameter of about 3.8 to 4.8.

9. Apparatus as claimed in claim 1 wherein said openings are distributed along a length of the tube equal to about ten centimeters from said chamber.

10. Apparatus as claimed in claim 9 comprising gradations along the tube adjacent the length in which the openings are located to enable ascertaining the depth of penetration of the tube.

11. Apparatus as claimed in claim 1 wherein the openings are staggered on opposite sides of the tube.

12. Apparatus as claimed in claim 9 wherein said tube is imperforate between the proximal end and the said length in which the openings are located.

* * * * *